(12) United States Patent
Davis

(10) Patent No.: US 6,940,000 B1
(45) Date of Patent: Sep. 6, 2005

(54) WOUND COVERING

(76) Inventor: Henry Davis, P.O. Box 666, Mukilteo, WA (US) 98275

( * ) Notice: Subject to any disclaimer, the term of this patent is extended or adjusted under 35 U.S.C. 154(b) by 81 days.

(21) Appl. No.: 10/408,180

(22) Filed: Apr. 8, 2003

(51) Int. Cl.[7] .............................................. A61F 5/00
(52) U.S. Cl. ..................... 602/42; 602/54; 128/888; 128/889
(58) Field of Search ............ 602/41–59; 606/213–216; 128/888, 889

(56) References Cited

U.S. PATENT DOCUMENTS

| 47,333 | A | | 4/1865 | Kleinschmidt | |
|---|---|---|---|---|---|
| 1,920,808 | A | * | 8/1933 | Sander | 128/888 |
| 2,221,758 | A | * | 11/1940 | Elmquist | 128/888 |
| 2,443,140 | A | * | 6/1948 | Larsen | 128/888 |
| 3,782,378 | A | * | 1/1974 | Page | 128/888 |
| 4,972,829 | A | * | 11/1990 | Knerr | 602/52 |
| 5,158,555 | A | | 10/1992 | Porzilli | |
| 5,364,339 | A | | 11/1994 | Carver | |
| 5,556,375 | A | * | 9/1996 | Ewall | 602/58 |
| 5,702,356 | A | * | 12/1997 | Hathman | 602/41 |
| 6,041,786 | A | | 3/2000 | DeLaTorre | |
| 6,343,604 | B1 | | 2/2002 | Beall | |
| 6,787,682 | B2 | * | 9/2004 | Gilman | 602/58 |
| 2002/0169405 | A1 | * | 11/2002 | Roberts | 602/43 |
| 2004/0127838 | A1 | * | 7/2004 | Jeziak | 602/43 |

* cited by examiner

*Primary Examiner*—Kim M. Lewis

(57) ABSTRACT

A wound covering includes a loop member including a peripheral wall that has an upper edge, a lower edge, an inner surface and an outer surface. The loop member defines an opening. A screen is attached to the loop member such that the screen extends across the opening. The screen comprises an air permeable and flexible material. A panel is attached to and extends along the peripheral wall of the loop member such that the panel does not extend over the opening. The panel comprises a flexible material having an upper surface and a lower surface. The lower surface faces the same direction as the lower edge of the loop member. An adhesive is positioned on the lower surface of the panel. The panel may be attached to a skin surface such that the loop member extends around a wound on the skin surface.

7 Claims, 3 Drawing Sheets

WOUND COVERING

BACKGROUND OF THE INVENTION

1. Field of the Invention

The present invention relates to bandage devices and more particularly pertains to a new bandage device for allowing air to circulate around a wound.

2. Description of the Prior Art

The use of bandage devices is known in the prior art. While these devices fulfill their respective, particular objectives and requirements, the need remains for a device that includes a covering that is positionable over and spaced from a wound such that air may circulate over and around the wound.

SUMMARY OF THE INVENTION

The present invention meets the needs presented above by including a loop member which is positionable around the wound. A covering, extending over an opening in the loop member, protects the wound from foreign material while allowing air to circulate around the wound.

Another object of the present invention is to provide a new bandage device that positions the covering from the wound so that the wound is not aggravated by the rubbing of the covering on the wound. This is particularly useful for wounds such as burns.

To this end, the present invention generally comprises a loop member including a peripheral wall that has an upper edge, a lower edge, an inner surface and an outer surface. The loop member defines an opening. A screen is attached to the loop member such that the screen extends across the opening. The screen comprises an air permeable and flexible material. A panel is attached to and extends along the peripheral wall of the loop member such that the panel does not extend over the opening. The panel comprises a flexible material having an upper surface and a lower surface. The lower surface faces the same direction as the lower edge of the loop member. An adhesive is positioned on the lower surface of the panel. The panel may be attached to a skin surface such that the loop member extends around a wound on the skin surface.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
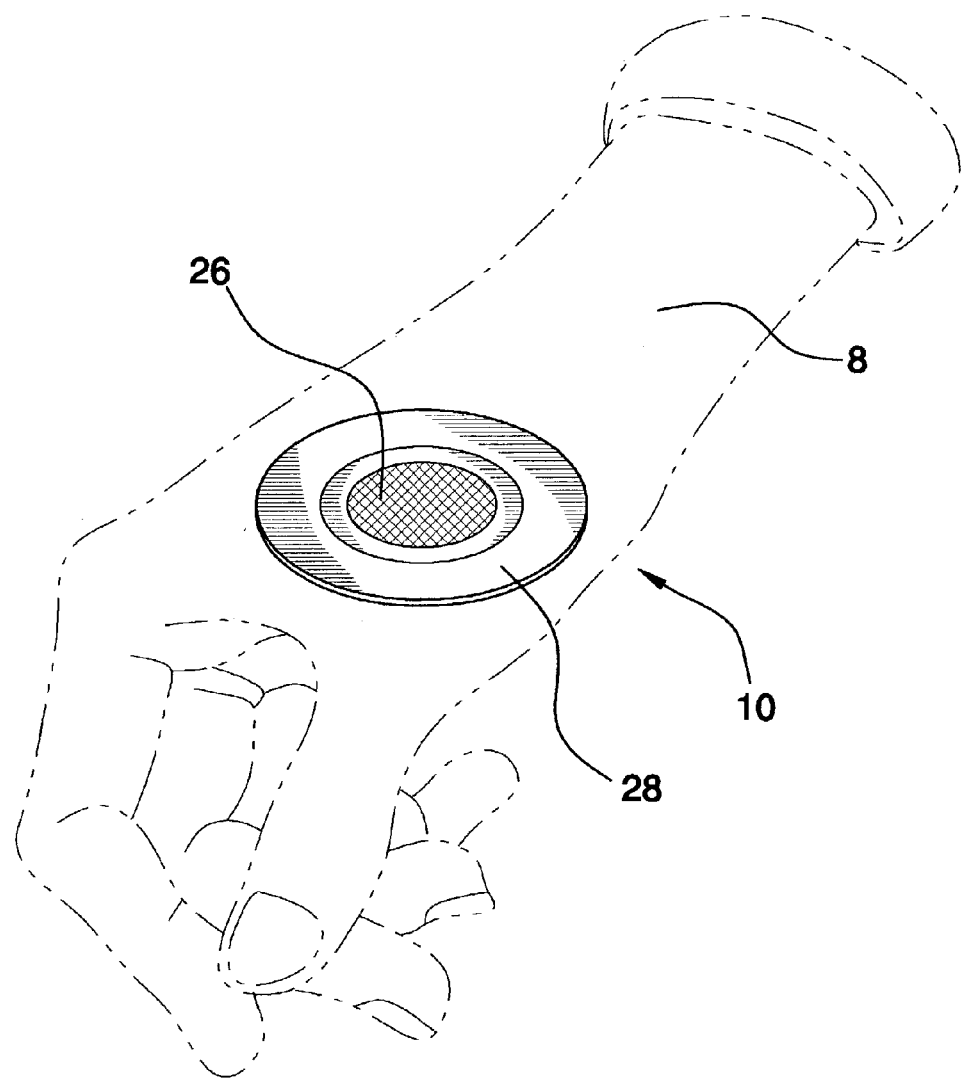
FIG. 1 is a schematic perspective in-use view of a wound covering according to the present invention.
Figure 2:
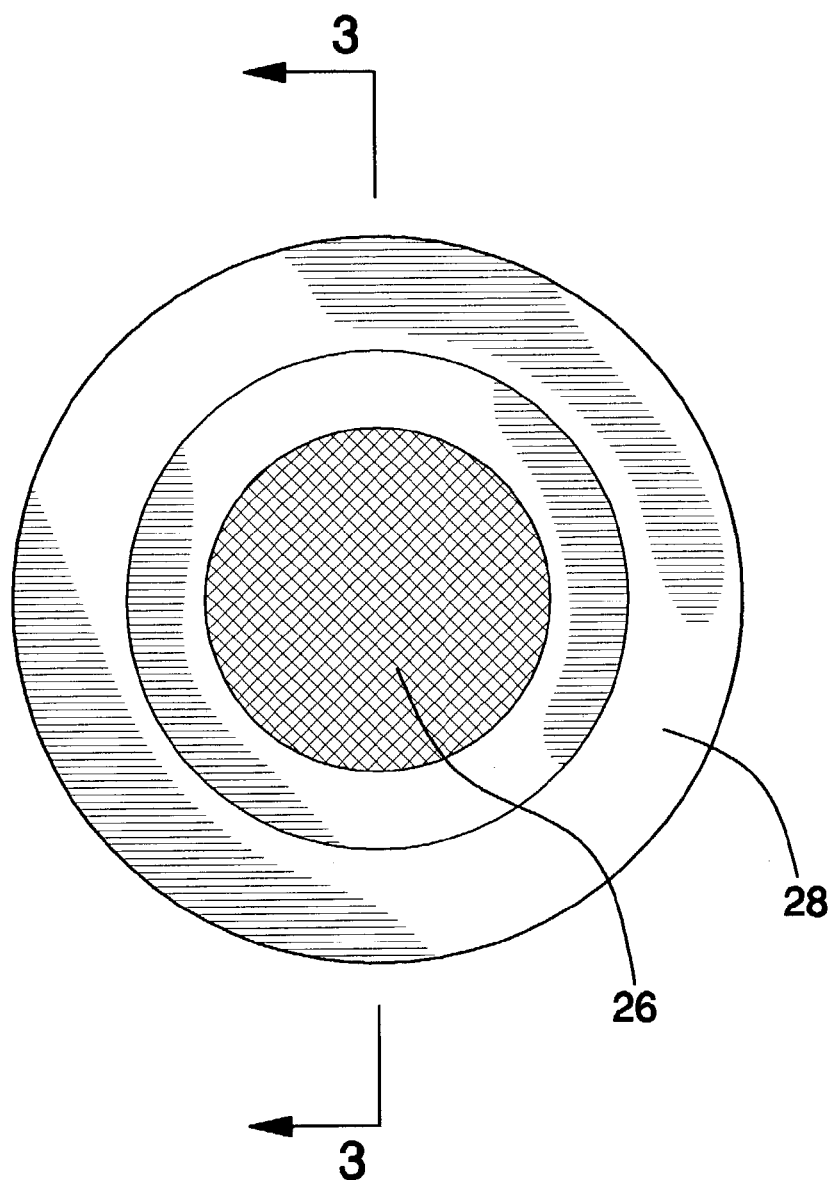
FIG. 2 is a schematic top plan view of the present invention.
Figure 3:
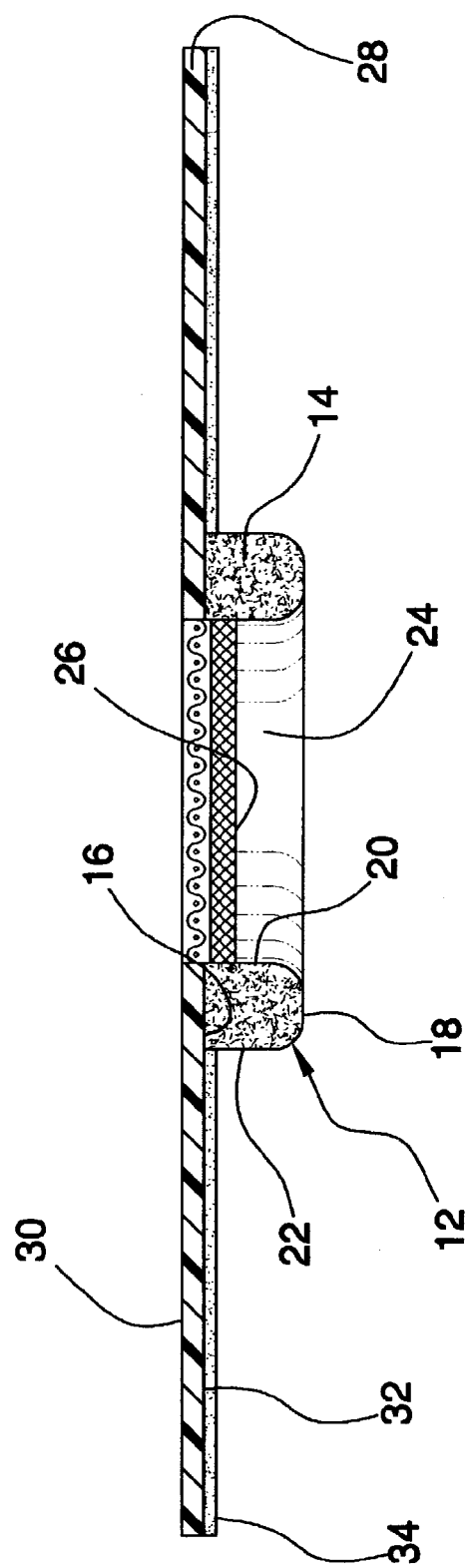
FIG. 3 is a schematic cross-sectional view taken along line 3—3 of FIG. 2 of the present invention.

With reference now to the drawings, and in particular to FIGS. 1 through 3 thereof, a new bandage device embodying the principles and concepts of the present invention and generally designated by the reference numeral 10 will be described.

As best illustrated in FIGS. 1 through 3, the wound covering 10 generally comprises a loop member 12 including a peripheral wall 14 having an upper edge 16, a lower edge 18, an inner surface 20 and an outer surface 22. The loop member 12 defines an opening 24 which extends through loop member 12. The loop member 12 comprises a flexible material which is preferably a foamed elastomeric material or a cotton material.

A screen 26 is attached to the loop 12 such that the screen 26 extends across the opening 24. The screen 26 comprises an air permeable and flexible material. The screen 26 extends along a perimeter of the inner surface 20 and is preferably positioned nearer the upper edge 16 than the lower edge 18. The screen 26 is preferably constructed of a mesh fine enough to allow air to pass therethrough but hinders debris, such as dust, from filtering therethrough. The screen 26 preferably comprises a cotton cloth material.

A panel 28 is attached to and extends along the peripheral wall 14 of the loop member 12 such that the panel 28 does not extend over the opening 24. The panel 28 comprises a flexible material having an upper surface 30 and a lower surface 32. The lower surface 32 faces in the same direction as the lower edge 18 of the loop member 12. The panel 28 is preferably attached to the upper edge 16 of the of the loop member 12 though it may be positioned anywhere on the peripheral wall 14. An adhesive 34 is positioned on the lower surface 32 of the panel 28. The adhesive 34 generally covers the lower surface 32.

In use, the panel 28 may be attached to a skin surface 8 such that the loop member 12 extends around a wound on the skin surface 8. The loop member 12, by extending around the wound, keeps the screen 26 spaced from the wound to prevent the rubbing of the screen 26 on the wound and allow air to circulate across the wound.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A wound covering device for covering a wound in a spaced relationship from the wound, said device comprising:

a loop member including a peripheral wall having an upper edge, a lower edge, an inner surface and an outer surface, an opening being defined by said loop member;

a screen being attached to said loop member such that said screen extends across said opening, said screen comprising an air permeable and flexible material;

a panel being attached to and extending along said peripheral wall of said loop member such that said panel does not extend over said opening, said panel extending completely around a circumference of loop member, said panel comprising a flexible material having an upper surface and a lower surface, said lower surface facing the same direction as said lower edge of said loop member;

an adhesive being positioned on said lower surface of said panel; and wherein said panel may be attached to a skin surface such that said loop member extends around a wound on the skin surface.

2. The wound covering device of claim 1, wherein said loop member comprises a flexible material.

3. The wound covering device of claim 1, wherein said screen is positioned nearer said upper edge than said lower edge.

4. The wound covering device of claim 3, wherein said panel is attached to said upper edge of said of said loop member.

5. The wound covering device of claim 1, said panel having a circular shape.

6. A wound covering device for covering a wound in a spaced relationship from the wound, said device comprising:

a loop member including a peripheral wall having an upper edge, a lower edge, an inner surface and an outer surface, an opening being defined by said loop member, said loop member comprising a flexible material;

a screen being attached to said loop member such that said screen extends across said opening, said screen comprising an air permeable and flexible material, said screen extending along a perimeter of said inner surface, said screen being positioned nearer said upper edge than said lower edge;

a panel being attached to and extending along said peripheral wall of said loop member such that said panel does not extend over said opening, said panel extending completely around a circumference of loon member, said panel comprising a flexible material having an upper surface and a lower surface, said lower surface facing the same direction as said lower edge of said loop member, said panel being attached to said upper edge of said loop member;

an adhesive being positioned on said lower surface of said panel, said adhesive generally covering said lower surface; and wherein said panel may be attached to a skin surface such that said loop member extends around a wound on the skin surface.

7. The wound covering device of claim 6, said panel having a circular shape.

* * * * *